US012527362B2

(12) United States Patent
Shreiner

(10) Patent No.: US 12,527,362 B2
(45) Date of Patent: Jan. 20, 2026

(54) HEAT TRANSFER GARMENT

(71) Applicant: Grant T. Shreiner, Lancaster, PA (US)

(72) Inventor: Grant T. Shreiner, Lancaster, PA (US)

( * ) Notice: Subject to any disclaimer, the term of this patent is extended or adjusted under 35 U.S.C. 154(b) by 0 days.

(21) Appl. No.: 18/941,196

(22) Filed: Nov. 8, 2024

(65) Prior Publication Data

US 2025/0151816 A1 May 15, 2025

Related U.S. Application Data

(60) Provisional application No. 63/599,152, filed on Nov. 15, 2023.

(51) Int. Cl.
*A41B 11/00* (2006.01)
*A61B 5/00* (2006.01)

(52) U.S. Cl.
CPC ............ *A41B 11/00* (2013.01); *A61B 5/6804* (2013.01)

(58) Field of Classification Search
CPC .............................. A41B 11/00; A61B 5/6804
See application file for complete search history.

(56) References Cited

U.S. PATENT DOCUMENTS

| | | | | |
|---|---|---|---|---|
| 10,492,543 | B2 | 12/2019 | Parnell | |
| 11,285,032 | B2 * | 3/2022 | Eugene | A41B 11/003 |
| 2016/0374411 | A1 * | 12/2016 | Brooks | A61F 7/007 165/104.21 |
| 2020/0113248 | A1 * | 4/2020 | Podolskiy | A41B 11/02 |
| 2020/0205483 | A1 * | 7/2020 | Burns | A41B 11/02 |
| 2025/0151816 | A1 * | 5/2025 | Shreiner | A41B 11/00 |

* cited by examiner

*Primary Examiner* — Khaled Annis
(74) *Attorney, Agent, or Firm* — Barley Snyder

(57) ABSTRACT

A garment having an upper portion having a cuff sector and a leg sector extending downwards from the cuff sector, the leg sector having a tapering funnel shaped section composed of copper, The garment further having a lower portion having a heel sector, a sole sector, an instep sector, and a toe sector. Heat will generate within the heel sector, the sole sector, the instep sector and the toe sector and transfer to the upper portion where the thermal energy and heat will disperse.

18 Claims, 7 Drawing Sheets

HEAT TRANSFER GARMENT

CROSS-REFERENCE TO RELATED APPLICATIONS

This application claims priority under 35 U.S.C. 119 to U.S. Provisional Patent Application No. 63/599,152 filed Nov. 15, 2023.

FIELD OF THE INVENTION

The present invention relates to a heat transfer garment and, more particularly, to a heat transfer garment for conversion of thermal energy within the garment.

BACKGROUND

In general, warm weather and summer sports are very popular. A plurality of activities is done during the summer months such as hiking, camping, baseball and soccer. In order for the user to endure and enjoy these activities, proper protection for the body is required which includes regulating the participant's body temperature. Particularly, protection of the user's feet is required when playing sports on hot surfaces such as turf fields.

When enduring warmer temperatures, an individual's feet is one of the most vulnerable spots that require proper regulation of heat. Accordingly, a need remains for providing the proper comfort and protection for regulating heat of the user's feet. As the foregoing illustrates, the invention provides a heat transfer garment.

SUMMARY

A garment includes an upper portion having a cuff sector having a fiber section composed of Cotton, Polyester, Nylon, Rubber and Copper. The leg sector extending downwards from the cuff sector, the leg sector includes the fiber section, the leg sector further includes a tapering funnel shaped section composed of double an amount of copper with respect to the fiber section. The lower portion having a heel sector, a sole sector, an instep sector and a toe sector, heat will generate within the heel sector, the sole sector, the instep sector and the toe sector, a double copper infused fiber section associated with the heel sector, the sole sector, the instep sector and the toe sector will receive thermal energy and transfer heat towards the leg sector and the cuff sector where the thermal energy will disperse.

BRIEF DESCRIPTION OF DRAWINGS

In the following, the present invention is described in more detail with references to the drawings in which.

DETAILED DESCRIPTION OF THE EMBODIMENT(S)

The present disclosure includes a heat transfer garment according to the invention. In the exemplary embodiment, the heat transfer garment generally includes an upper portion 2 and a lower portion 4.

Figure 1:
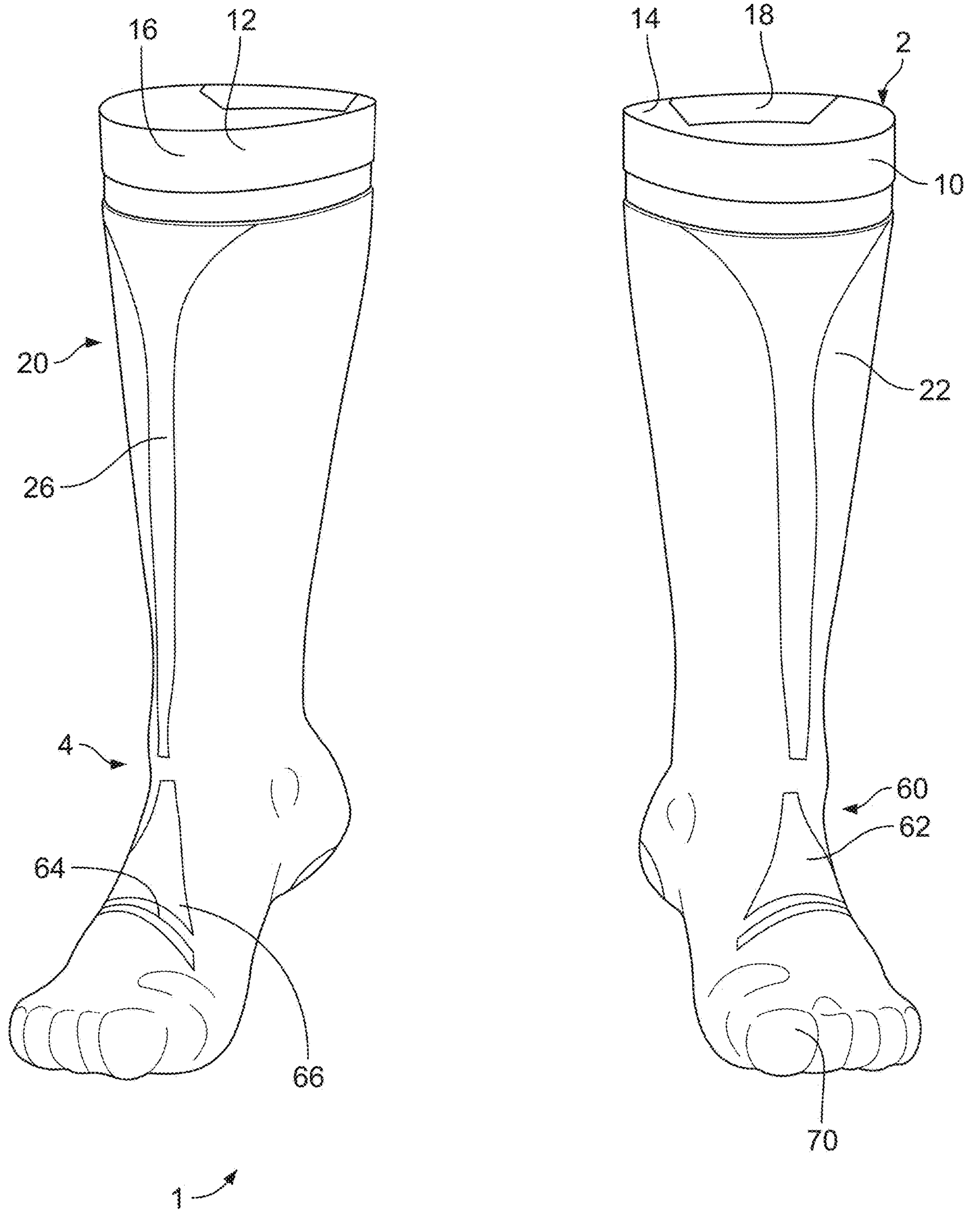
FIG. 1 illustrates a front perspective view of the invention.
Figure 2:
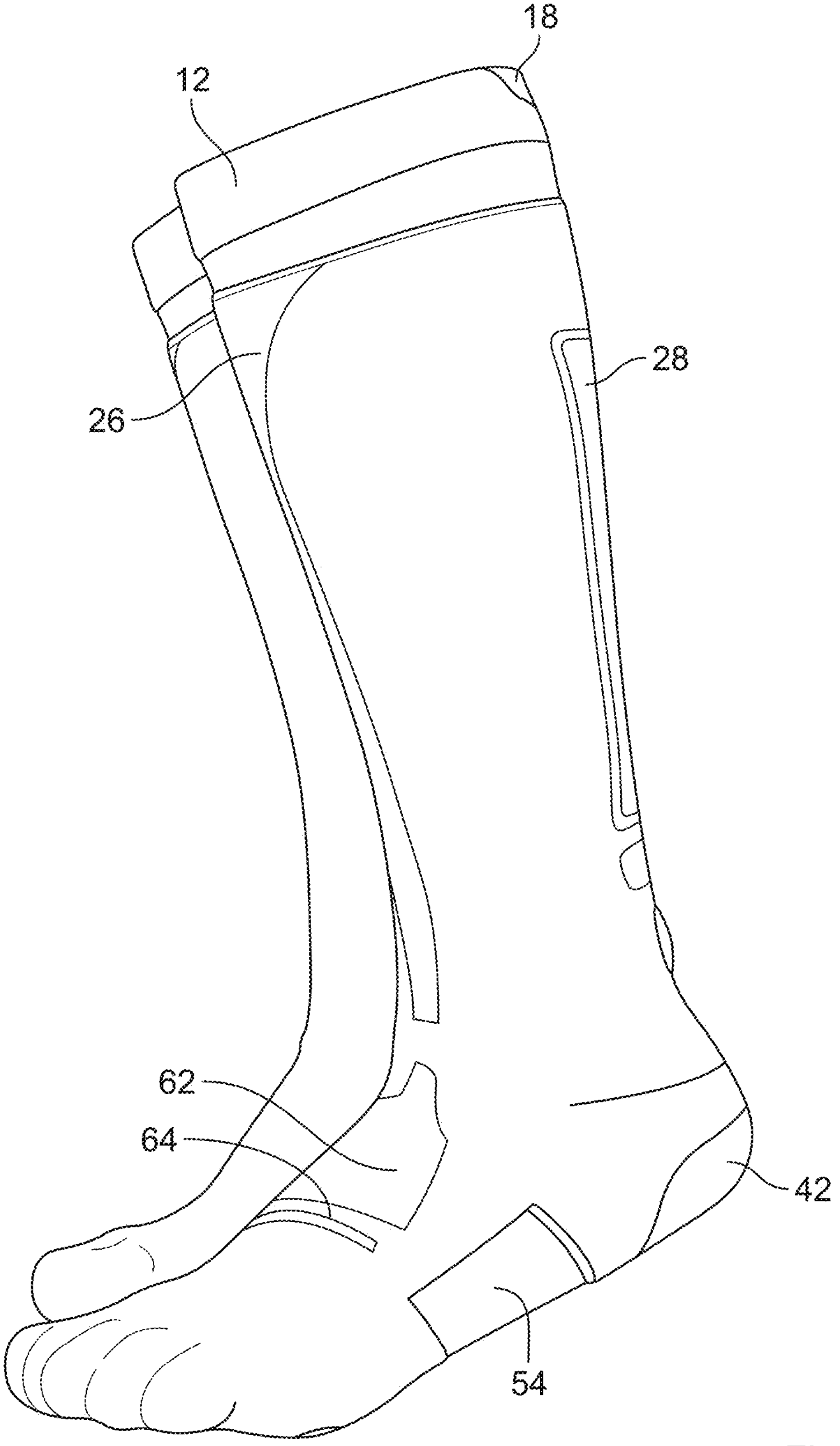
FIG. 2 illustrates a left side perspective view of the invention of FIG. 1.
Figure 3:
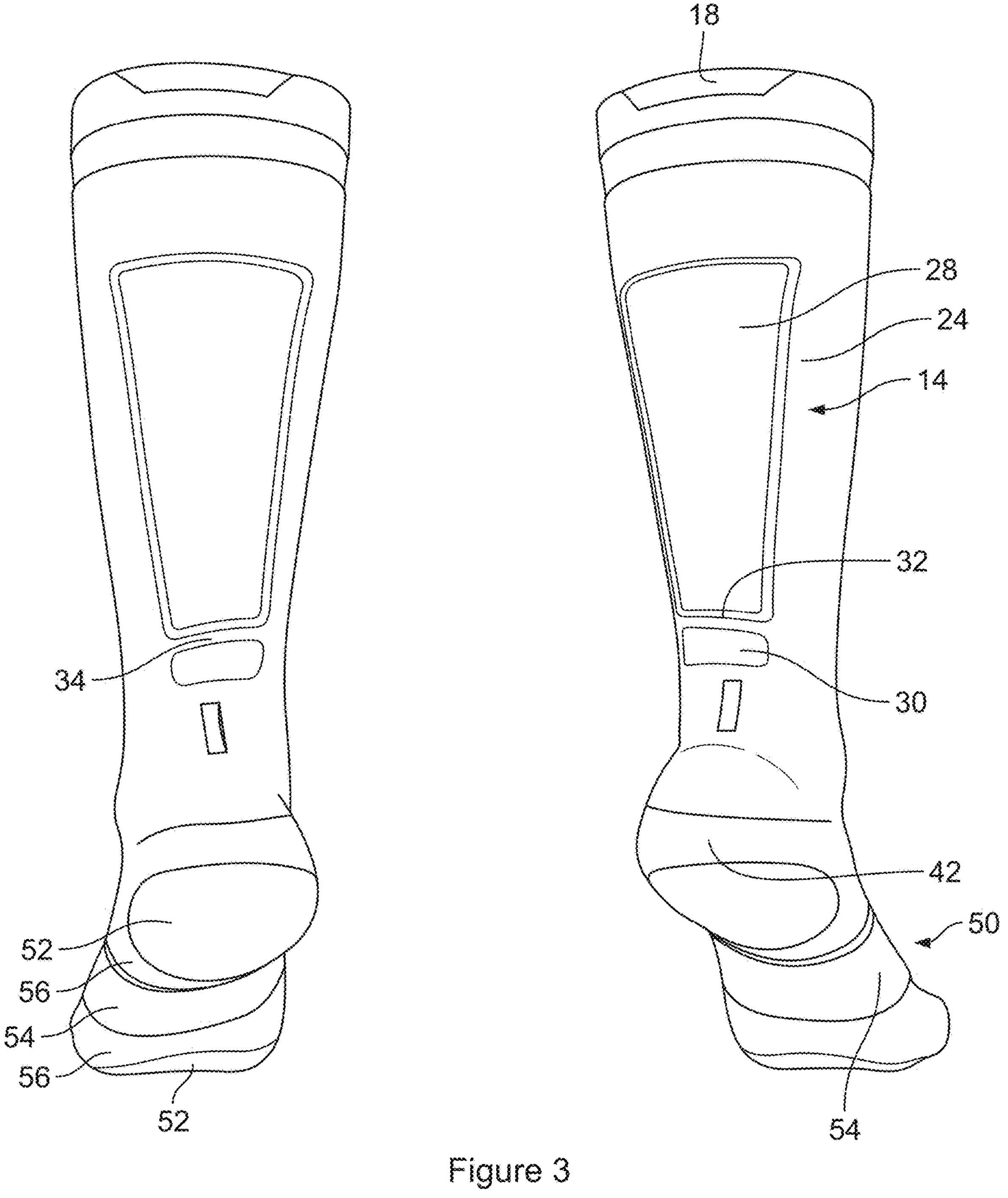
FIG. 3 illustrates a rear perspective view of the invention of FIG. 2.
Figure 4:
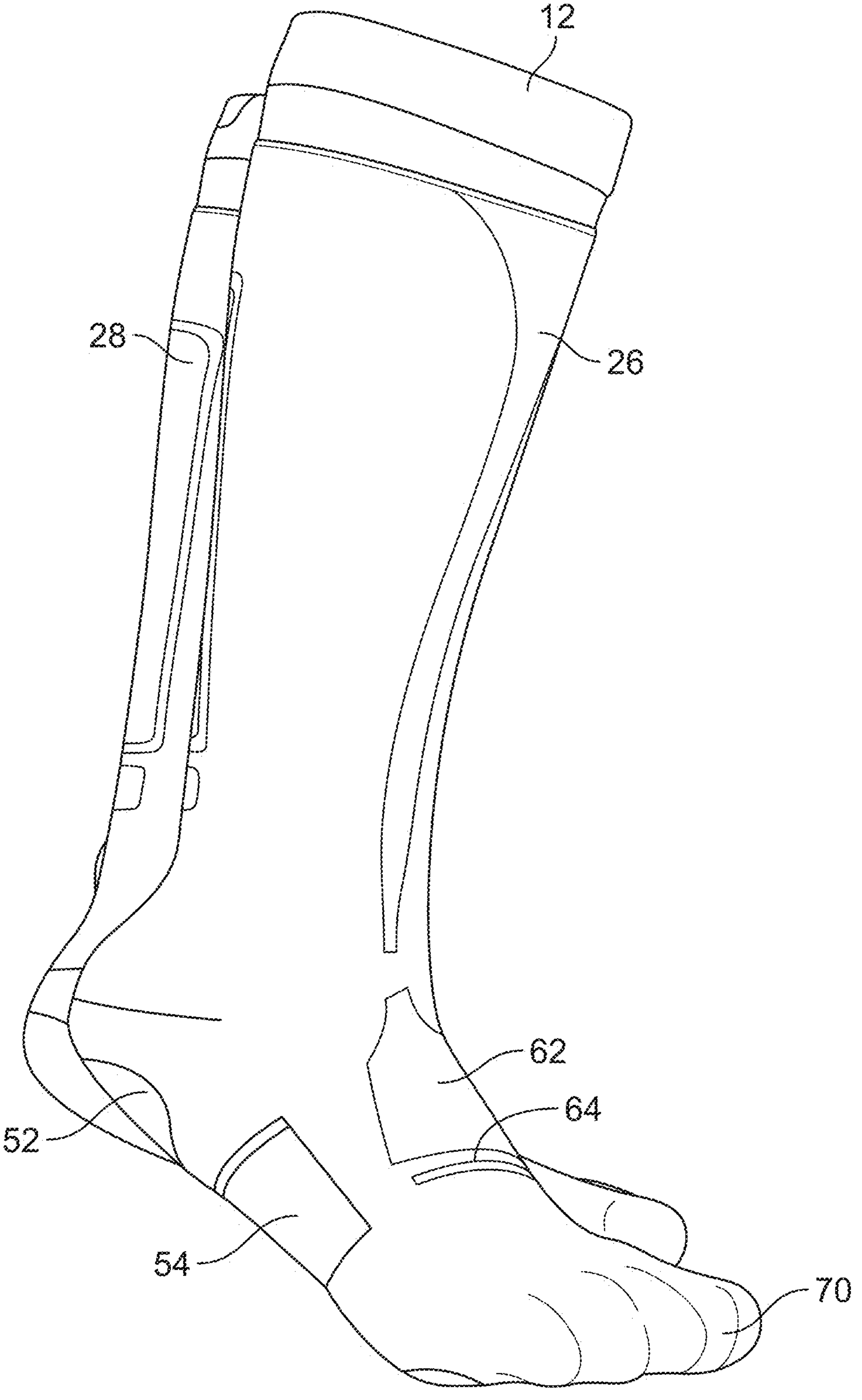
FIG. 4 illustrates a right side perspective view of the invention of FIG. 3.
Figure 5:
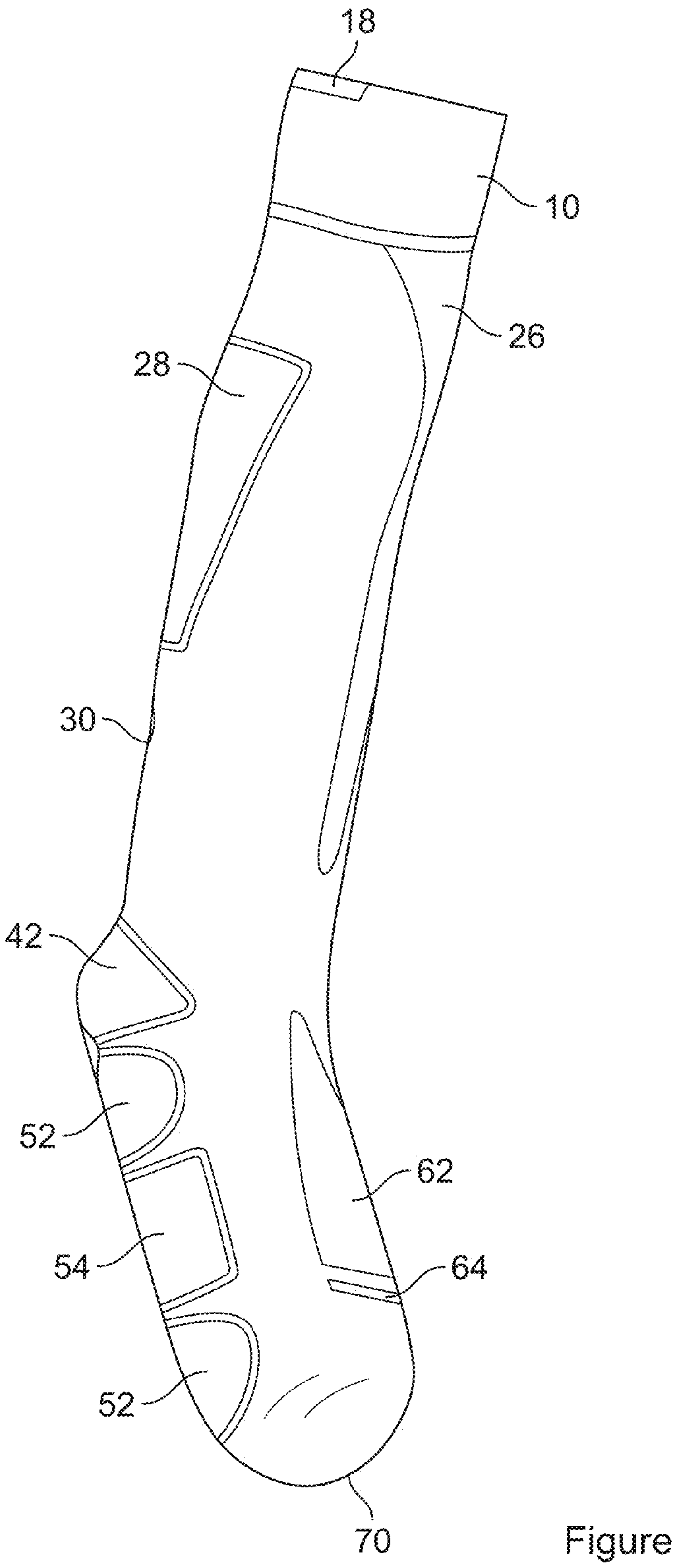
FIG. 5 illustrates another right side perspective view of the invention of FIG. 4.
Figure 6:
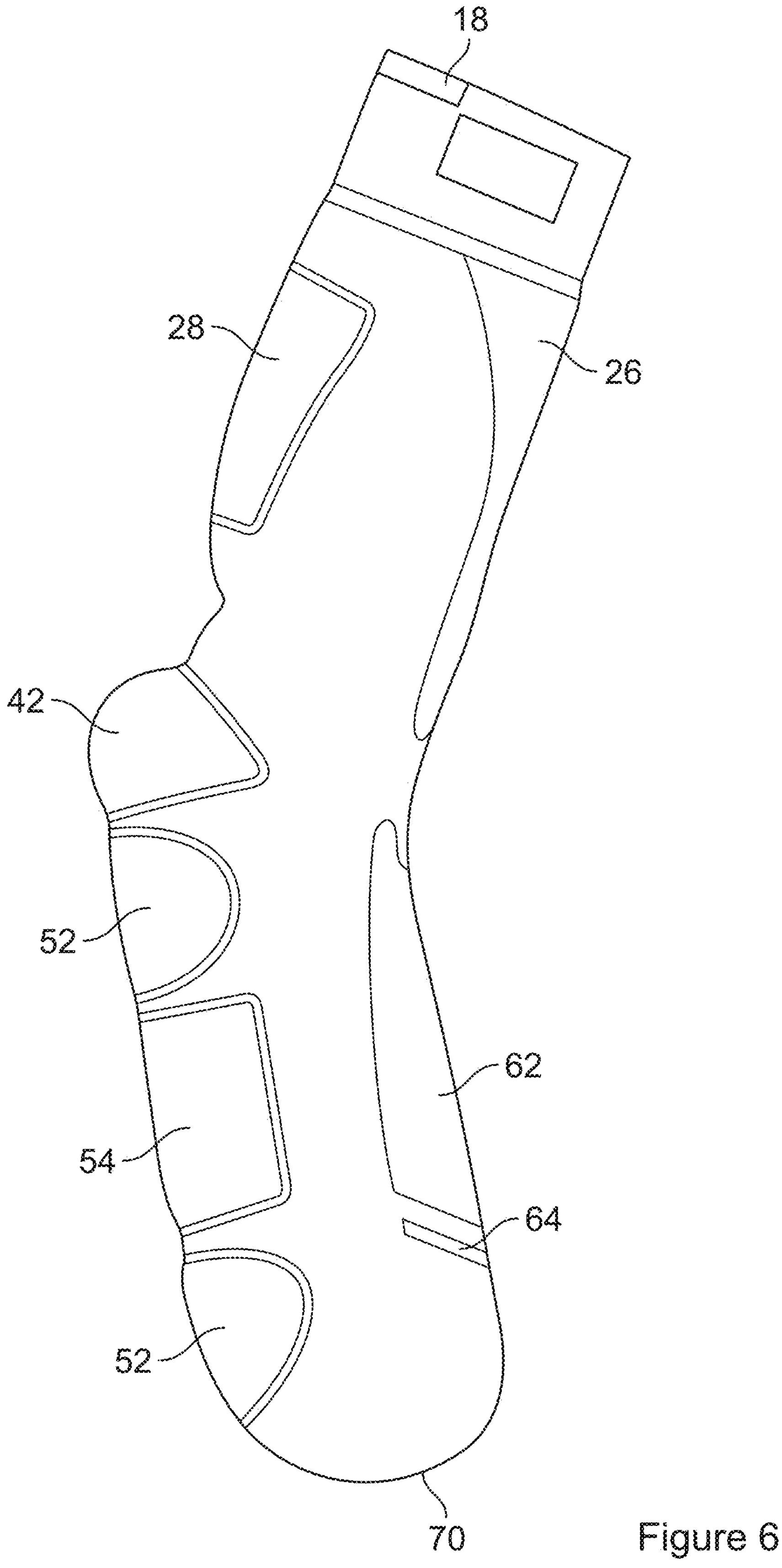
FIG. 6 illustrates another right side perspective view of the invention of FIG. 5.
Figure 7:
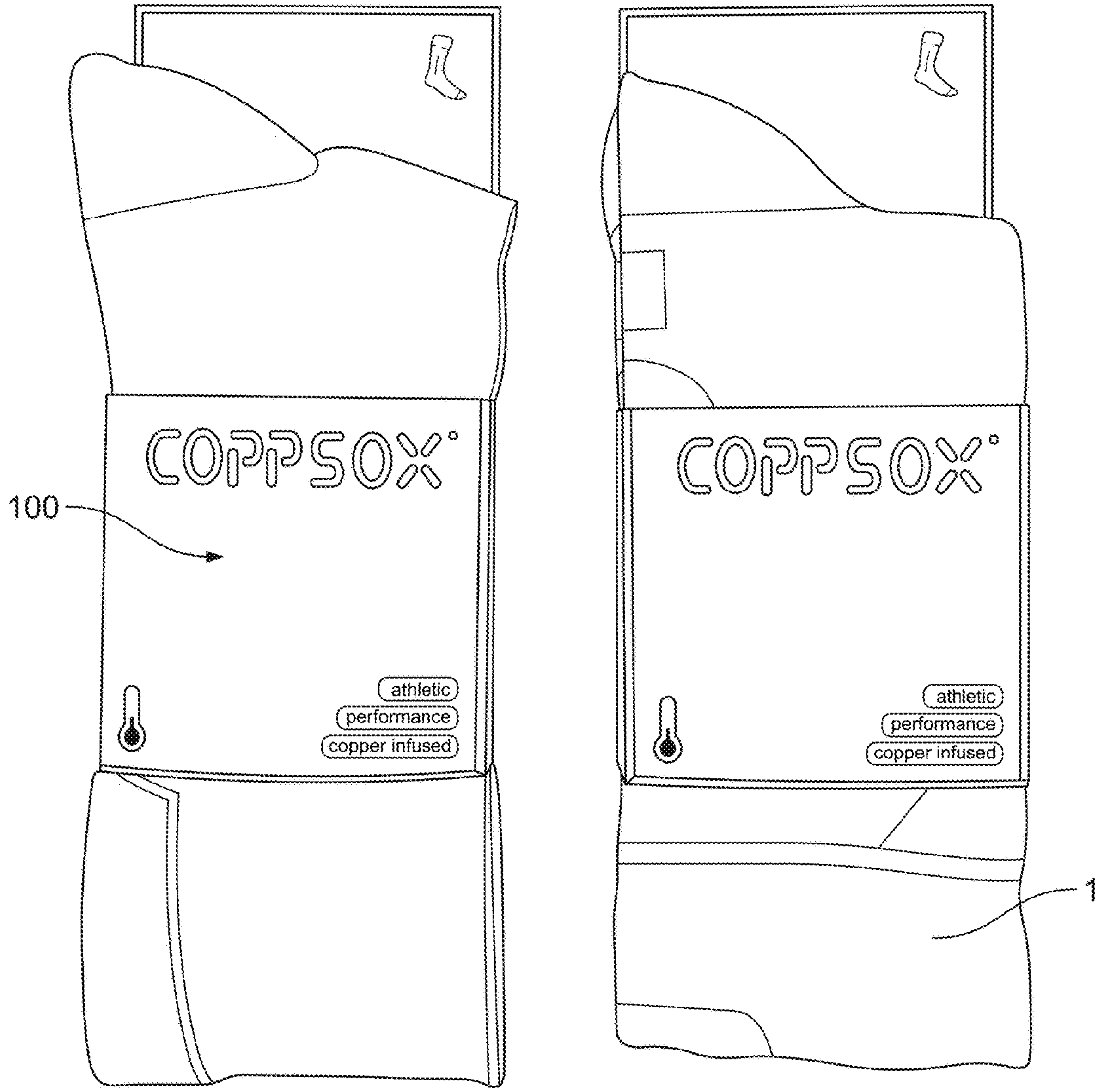
FIG. 7 illustrates the invention in a packaging.

With reference to FIGS. 1-7, the upper portion 2 of the heat transfer garment 1 includes a cuff sector 10 and a leg sector 20.

In the exemplary embodiment, the cuff sector 10 is an elongated member, specifically the cuff sector 10 is cylindrically shaped. The cuff sector 10 further stretches and decompresses when receiving a user's foot.

In the exemplary embodiment, the cuff sector 10 further includes a frontal portion 12 and a rearward portion 14. The frontal portion 12 includes a fiber section 16 composed of Cotton, Polyester, Nylon and Rubber. Specifically, the fiber section 16 is composed of 57.5% Cotton, 25.7% Polyester, 9.4% Nylon, 6.3% Rubber, and 1.1% Spandex. One skilled in the art would understand the applicant's composition of materials is not the exclusive embodiment of the invention. In another exemplary embodiment, the fiber section 16 includes the addition of copper. Specifically, 394 parts per million in copper. In another embodiment, the composition may be 82 parts per million in copper.

The rearward portion 14 includes an elongated member 18, specifically a trapezoidal shaped elongated member. A perimeter of the elongated member 18 is composed of double the amount of concentrated copper added to the fiber section 16. One skilled in the art would understand the applicant's design is not the exclusive embodiment. An area of the elongated member 18 is composed of the fiber section 16 as discussed previously.

In the exemplary embodiment, with reference to FIGS. 1-7, the leg sector 20 is an elongated member extending downwards from the cuff sector 10. Specifically, the leg sector 20 is cylindrically shaped. The leg sector 20 includes a frontal portion 22 and a rearward portion 24.

The leg sector 20 further includes a funnel shaped section 26 positioned on the frontal portion 22. The funnel shaped section 26 extends downwards, specifically tapering as the funnel shaped section 26 extends down the frontal portion 22 of the leg sector 20. The funnel shaped portion 26 is composed of copper, specifically, an entire area of the funnel shaped portion 26 is composed of double the amount of concentrated copper compared to the fiber section 16.

The leg sector 20 further includes the fiber section 16 encompassing an area around the funnel shaped portion 26. Specifically, the fiber section 16 extends almost the entire area of the frontal portion 12.

The leg sector 20 further includes a rectangular shaped portion 28. The rectangular shaped portion 28 extends downwards, specifically tapering down the rearward portion 14 of the leg sector 20. A perimeter of the rectangular shaped portion 28 is composed of double the amount of copper compared to the fiber section 16. One skilled in the art would understand the applicant's design and placement of copper is not the exclusive embodiment.

The leg sector 20 further includes an oblong shaped portion 30. The oblong shaped portion 30 extends a width of a lower sector 32 of the rectangular shaped portion 28. A perimeter of the oblong shaped portion 30 is composed of double the amount of concentrated copper compared to the fiber section 16. One skilled in the art would understand the applicant's design and placement of the copper is not the exclusive embodiment.

The leg sector 20 further includes a gap 34 formed between the rectangular shaped portion 28 and the oblong shaped portion 30. The gap 34 is composed of the fiber section 16 as previously described above. Additionally, the fiber section 16 surrounds an inner side 36 and an outer side 38 of the perimeter of both the rectangular shaped portion 28 and the oblong shaped portion 30.

In an exemplary embodiment, with reference to FIGS. 1-7, a lower portion 4 includes a heel sector 42, a sole sector 50, an instep sector 60 and a toe sector 70.

The heel sector 42 is a circular member. Specifically, the heel sector 42 is sculpted to a heel of the user's foot. A perimeter of the heel sector 42 is composed of double the amount of concentrated copper compared to the fiber section 16. One skilled in the art would understand the shape of the heel sector 42 is not the exclusive embodiment. An area inside the heel sector 42 is composed of the fiber section 16.

In the exemplary embodiment, the sole sector 50 is an elongated member, specifically the sole sector 50 is semi-cylinder shaped. With reference to the figures, the sole sector 50 includes a pair of oval shaped sectors 52. The at least two oval shaped sectors 52 extend a width of the sole sector 50. One skilled in the art would understand the shape of each of the oval shaped sectors 52 is not the exclusive embodiment of the invention. A perimeter of each of the oval shaped sectors 52 is composed of double the amount of concentrated copper compared to the fiber section while an area inside the oval shaped sector 52 is composed of only the fiber section 16.

The sole sector 50 further includes a square shaped sector 54 positioned between the pair of oval shaped sectors 52. The square shaped sector 54 extends the width of the sole sector 50. One familiar with the art would understand the shape of the square shaped sector 54 is not the exclusive embodiment of the invention. A perimeter of the square shaped sector 54 is composed of the double amount of concentrated copper compared to the fiber section while an area inside the square shaped sector 54 is composed of the fiber section 16.

The sole sector 50 further includes a gap 56 positioned between the oval shaped sectors 52 and the square shaped sector 54. One skilled in the art would understand the arrangement of the oval shaped sectors 52 and the square shaped sector 54 are not the exclusive embodiment of the invention. The gap 56 is further composed of the fiber section 16.

In the exemplary embodiment, the instep sector 60 is an elongated member, specifically, the instep sector 60 is an inverted semi-cylinder shape. The instep sector 60 includes a triangular shaped sector 62. The triangular shaped sector 62 thickens in width while extending down the instep sector 60. One familiar with the art would understand the applicant's design is not the exclusive embodiment. The triangular shaped sector 62 is composed of double the amount of concentrated copper compared to the fiber section. Specifically, an entire area of the triangular shaped sector 62 is composed of the double amount of concentrated copper.

The instep sector 60 further includes an elongated cylindrical shaped sector 64. The elongated cylindrical shaped sector 64 extends a width of a base 66 of the triangular shaped sector 62. The elongated cylindrical shaped sector 64 is composed of the double amount of concentrated copper compared to the fiber section. Specifically, an entire area of the cylindrical shaped sector 64 is composed of the double amount of concentrated copper.

The toe sector 70 is a semicircular member. Specifically, the toe sector 70 flexes to mold to a user's toes.

In the exemplary embodiment, the sections of the garment 1 that include the double amount of copper will receive a majority of the heat while the fiber section 16 with the singular amount of copper will permit an easier transfer of heat. When a user utilizes the heat transfer garment, heat will generate within the heel sector 42, the sole sector 50, the instep sector 60 and the toe sector 70. The copper infused fiber sections will receive the thermal energy and transfer the heat towards the leg sector 20 and the cuff sector 10. The copper infused fiber sections of the leg sector 20 will receive the thermal energy and transfer the thermal energy towards the copper infused fiber section of the cuff sector 10. The thermal energy will then disperse as it moves up the leg, and exchanges warmer temperatures for cooler temperatures from movement and being further away from the heat source, thereby cooling the user's foot.

In the exemplary embodiment, the heat transfer garment 1 will be positioned in a packaging 100.

It should be noted that various changes and modifications to the embodiments described herein will be apparent to those skilled in the art. Such changes and modifications may be made without departing from the spirit and scope of the present invention and without diminishing its intended advantages. For example, various embodiments of the systems and methods may be provided based on various combinations of the features and functions from the subject matter provided herein.

What is claimed is:

1. A garment, comprising:
- an upper portion having:
  - a cuff sector having a fiber section composed of Cotton, Polyester, Nylon, Rubber and Copper;
  - a leg sector extending downwards from the cuff sector, the leg sector includes the fiber section, the leg sector further includes a tapering funnel shaped section composed of double an amount of copper with respect to the fiber section; and
- a lower portion having:
  - a heel sector;
  - a sole sector;
  - an instep sector; and
  - a toe sector, heat will generate within the heel sector, the sole sector, the instep sector and the toe sector, a double copper infused fiber section associated with the heel sector, the sole sector, the instep sector and the toe sector will receive thermal energy and transfer heat towards the leg sector and the cuff sector where the thermal energy will disperse.

2. The garment of claim 1, wherein the cuff sector includes a frontal portion and a rearward portion.

3. The garment of claim 2, wherein each section composed of copper is 394 parts per million in copper.

4. The garment of claim 3, wherein the leg sector further includes a frontal portion and a rearward portion.

5. The garment of claim 4, wherein the tapering funnel shaped section is positioned on the frontal portion.

6. The garment of claim 5, wherein the leg sector further includes a rectangular shaped portion.

7. The garment of claim 6, wherein a perimeter of the rectangular shaped portion is composed of double an amount of copper compared to the fiber section.

8. The garment of claim 7, wherein the leg sector further includes an oblong shaped portion adjacent a lower sector of the rectangular shaped portion.

9. The garment of claim 8, wherein a perimeter of the oblong shaped portion is composed of double an amount of copper compared to the fiber section.

10. The garment of claim 9, wherein a gap is formed between the rectangular shaped portion and the oblong shaped portion.

11. A garment, comprising:

an upper portion having:

a cuff sector having:

a frontal section with a fiber section composed of Cotton, Polyester, Nylon, Rubber and Copper;

a rearward section with a composition of double an amount of copper compared to the fiber section;

a leg sector includes the fiber section encompassing a tapering funnel shaped section, the tapering funnel shaped section is composed of double an amount of copper compared to the fiber section; and a lower portion having:

a circular heel sector composed of the fiber section, a perimeter of the circular heel sector is composed of double an amount of copper compared to the fiber section;

a sole sector composed of the fiber section, having a square shaped sector positioned between a pair of oval shaped sectors, a perimeter of the square shaped sector and the pair of oval shaped sectors are composed of double an amount of copper compared to the fiber section;

an instep sector is composed of copper; and a toe sector.

12. The garment of claim 11, wherein thermal energy and heat generated within the lower portion is transferred through copper to the upper portion where the heat is dispersed.

13. The garment of claim 12, wherein the instep sector includes a triangular shaped sector.

14. The garment of claim 13, wherein the instep sector includes a cylindrical shaped sector.

15. The garment of claim 14, wherein the leg sector further includes a rectangular shaped sector opposing the tapering funnel shaped sector.

16. The garment of claim 15, wherein the rectangular shaped sector tapers away from the cuff sector.

17. The garment of claim 16, wherein the triangular shaped sector is composed of double an amount of copper compared to the fiber section.

18. The garment of claim 17, wherein the cylindrical shaped sector is composed of double an amount of copper compared to the fiber section.

* * * * *